(12) United States Patent
Liao

(10) Patent No.: US 8,507,495 B2
(45) Date of Patent: Aug. 13, 2013

(54) SENSITIZER, KIT AND USE FOR CANCER THERAPY

(75) Inventor: Pei-Ru Liao, Taipei (TW)

(73) Assignee: Uropro Biotech Co., Ltd., Taipei (TW)

( * ) Notice: Subject to any disclaimer, the term of this patent is extended or adjusted under 35 U.S.C. 154(b) by 3 days.

(21) Appl. No.: 13/238,601

(22) Filed: Sep. 21, 2011

(65) Prior Publication Data

US 2012/0214835 A1  Aug. 23, 2012

(30) Foreign Application Priority Data

Feb. 23, 2011 (TW) .............................. 100106084 A

(51) Int. Cl.
*A61K 31/4965* (2006.01)
*A61K 31/44* (2006.01)

(52) U.S. Cl.
USPC ..................................... 514/253.06; 514/291

(58) Field of Classification Search
USPC ........................................... 514/253.06, 291
See application file for complete search history.

(56) References Cited

U.S. PATENT DOCUMENTS

2006/0264384 A1  11/2006  Johansen et al.

FOREIGN PATENT DOCUMENTS

WO  WO 2010/132233 A1  11/2010

OTHER PUBLICATIONS

Sasaki et al., "Chloroquine potentiates the anti-cancer effect of 5-fluorouracil on color cancer cells," BMC Cancer, 2010, vol. 10:370, pp. 1-11.
Hartman et al., "Combined treatment with cisplatin and sirolimus to enhance cell death in human mesothelioma," The Journal of Thoracic and Cardiovascular Surgery, vol. 139, No. 5, pp. 1233-1240.

*Primary Examiner* — Raymond Henley, III
(74) *Attorney, Agent, or Firm* — Muncy, Geissler, Olds & Lowe, PLLC

(57) ABSTRACT

A cancer therapy sensitizer is disclosed. The cancer therapy sensitizer includes rapamycin and substituted quinoline. The present invention discloses a cancer therapy sensitization kit containing the two aforementioned compounds and a use of a combination of the two aforementioned compounds as a cancer therapy sensitizer as well. The application of the cancer therapy sensitizer, the kit and the use of the present invention is advantageous for improving the treatment effect of cancer therapies.

26 Claims, 3 Drawing Sheets

SENSITIZER, KIT AND USE FOR CANCER THERAPY

CROSS REFERENCE TO RELATED APPLICATIONS

This Non-provisional application claims priority under 35 U.S.C. §119(a) on Patent Application No(s). 100106084 filed in Taiwan, Republic of China on Feb. 23, 2011, the entire contents of which are hereby incorporated by reference.

BACKGROUND OF THE INVENTION

1. Field of Invention

The present invention relates to a sensitizer, a pharmaceutical composition, a kit and use. More particularly, the present invention relates to a sensitizer, a pharmaceutical composition, a kit and use for cancer therapy.

2. Related Art

Rapamycin, also known as sirolimus, was isolated from *Streptomyces hygroscopicus* of the soil sample obtained from Easter Island. Rapamycin has demostrated anti-fungal activity both in vitro and in vivo, especially in *Candida albicans*, and thus is used as an agricultural antifungal agent in the early days. However, when the fact that rapamycin has an inhibition effect against immunoreaction and anti-proliferative effect has been discovered, rapamycin is used on large scale as an immuno-inhibition drug, to inhibit the rejection of, for example, acute allotransplantation.

There are a variety of commercial drugs containing rapamycin now, for example, RAPAMUNE® (Wyeth, Collegeville, Pa., USA), the main use of which is for preventing organ rejection after kidney transplant. In addition, CERTICAN® produced by Novartis, East Hanover, N.J., USA, also provides the effect of preventing organ rejection.

On the other hand, chloroquine is a substituted quinoline which has been commonly used for over 60 years for the prevention and treatment of malaria prophylaxis, or for rheumatoid arthritis treatment and HIV treatment.

It has been testified that rapamycin and chloroquine has certain degree of treatment effect on a cancer and a tumor due to their property of inhibiting cell growth and inducing cell death. Relative research is also revealed in various international journal articles. In addition, the technique of combining rapamycin and chloroquine to inhibit the growth and proliferation of tumor has been disclosed in both US patent 2006/2064384 and WO patent 2010/132233.

However, the follow-up studies did not make any further breakthrough, and comparing to using individually, the use of their combination does not show obviously promoted effects. Moreover, when using in certain type of cancers, the treatment effects of using rapamycin, chloroquine and their combination are almost the same and show no advantage of combination use. On the other hand, there has been no report or article of using a combination of rapamycin and substituted quinoline as a sensitizer of cancer treatment, instead of a therapeutically active composition.

SUMMARY OF THE INVENTION

In view of the deficiency of prior art, the present invention is developed. An objective of the present invention is to provide a cancer therapy sensitizer, a pharmaceutical composition, a kit and use, which can substantially improve the treatment effect of the active composition in a cancer therapy by using the combination of rapamycin and substituted quinoline.

A cancer therapy sensitizer according to the present invention includes rapamycin and substituted quinoline. Preferably, the cancer therapy sensitizer comprises an effective amount of rapamycin and substituted quinoline, a pharmaceutically acceptable carrier, diluent, excipient or a combination thereof.

A cancer therapy sensitizer kit according to the present invention includes rapamycin and a first pharmaceutically acceptable carrier, diluent, excipient, or a combination thereof; and substituted quinoline and a second pharmaceutically acceptable carrier, diluent, excipient, or a combination thereof.

A use of a combination of a rapamycin and a substituted quinoline according to the present invention is as a cancer therapy sensitizer.

In order to demonstrate the technical features of the present invention in the follow-up contents, specific terms are defined hereunder, and the detail of the present invention will be illustrated thereafter. In addition, the cancer therapy sensitizer comprises both rapamycin and substituted quinoline, therefore, when a combination of rapamycin and quinoline is mentioned in the specification, it is considered to include the cancer therapy sensitizer and the product of the preparation of a cancer therapy sensitizer kit.

As used herein, a "cancer therapy sensitizer" refers to a composition containing at least two materials. Preferably, it refers to a composition containing an effective amount of two materials and a pharmaceutically acceptable carrier, diluent, excipient or a combination thereof. For example, the aforementioned composition can be applied before, during or both before and during the cancer therapy to improve or enhance the effect of one or more effective amount of therapeutically active composition upon a cancer or a tumor in an individual in need, and then achieve the goal of eliminating, inhibiting, improving, comforting or preventing a cancer and its symptoms; retarding, prohibiting, reversing the rate of tumor proliferation; or the medical effects similar to the foregoing goals. Wherein the composition mentioned above can be a combination of rapamycin and substituted quinoline. A cancer therapy method can be, for example, irradiating the lesion of a cancer or a tumor with an effective dose of radiation, or providing an effective amount of therapeutically active composition.

[Rapamycin]

As used herein, "rapamycin" refers to one selected from a group of compounds containing basic rapamycin structure (Formula I), including the derivatives obtained from chemical/biological modification or substitution, while still maintaining the nature of the original basic rapamycin structure or possessing similar properties with that of the original basic rapamycin structure. Therefore, "rapamycin" substantially comprises easters, ethers, enzymes, hydrazones, hydroxylamines, and rapamycins with the functional groups of the basic rapamycin structure modified by reduction, oxidation or substitution. Needless to say, "rapamycin" also includes pharmaceutically acceptable salts formed from the acidic/basic bases of Formula I.

Formula I

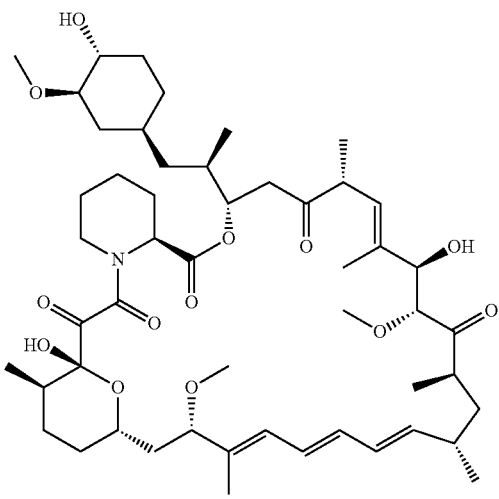

Rapamycin is referred to sirolimus, which is well-known in the present field, and it also comprises other compounds with identical or similar structures but different trade names. Further, except rapamycin, it is also proper for the present invention to use a compound selected from the group consisting of everlimus, temsirolimus, tacrolimus, 2-(dimethyl phosphinyl)sirolimus (deforolimus), biolimus and (42S)-42-deoxy-42-(1H-tetrazol-1-yl)-rapamycin (zotarolimus).

[Substituted Quinoline]

As used herein, "substituted quinoline" not only refers to chloroquine, but also includes, but not confines to, derivatives or chloroquine homologue obtained by further modification or substitution of chloroquine. Among which, derivatives obtained by further modification or substitution of chloroquine can possess the chemical structure of chloroquine, but one or more hydrogens or functional groups thereof are modified or substituted by one or more substituents. Specifically, the substituents mentioned above can be halogen, $C_{1-10}$ alkyl, $—OC_{1-10}$ alkyl, hydroxyl, $C_{6-10}$ aryl, heteroaryl, heterocycloalkyl, alkheterocycloalkyl, heteroalkyl or alkheteroalkyl. For example, substituted quinoline can be selected from a group consisting of free hydroxychloroquine, primaquine, amoproquine, amodiaquine, cycloquine, sontoquine, quinacrine, tebuquine and bis-pyroquine.

[Compound]

All of the compounds or materials, which are mentioned herein and substantially related to the technical feature of present invention, include the compounds or materials themselves and any pharmaceutically acceptable forms thereof. Among which, the pharmaceutically acceptable forms can be exemplified, but not limited to, various isomers including diastereomers and enantiomers, salts, ionization forms, solvent, prodrug, polymorph and racemic mixture.

[Ratio and Usage]

For the combination of rapamycin and substituted quinoline to perform sensitizing effects, the weight percentage ratio of an effective amount of rapamycin and substituted quinoline can be between about $1:6\times10^8$ and about 2000:1. However, the sensitizing effect of different ratio within the scope can be greatly different, thus, the advisable ratio of application is between about 1:100 and about 1:5000, preferably is between about 1:1000 and about 1:3000, more preferably is about 1:2000. Needless to say, said ratio can also be applied to the pharmaceutical composition of the present invention, or can be used as the preparation ratio of the cancer therapy sensitizer of the present invention when it is used in practice.

An example according to the ratio stated above is described hereinbelow. When the combination of rapamycin and substituted quinoline are prepared as a solution form for oral administration or injection, the effective amount of rapamycin may range from about 1 pg/ml to about 1 μg/ml, and the effective amount of substituted quinoline may range from about 0.5 ng/ml to about 0.6 mg/ml. Preferably, the effective amount of rapamycin may range from about 100 pg/ml to about 10 ng/ml, and the effective amount of substituted quinoline may range from about 10 ng/ml to about 15 μg/ml.

A combination of rapamycin and substituted quinoline is preferred, but not limited, to be used in a chemical treatment or a radiation treatment. These two are illustrated individually hereunder as representatives.

When applying the present invention to a chemical treatment, a combination of rapamycin and substituted quinoline can be administrated together with one or more effective amount of therapeutically active composition to improve or enhance the effect of the therapeutically active composition upon a cancer or a tumor in an individual in need.

When applying the present invention to a radiation treatment, a combination of rapamycin and substituted quinoline can be provided together with one or more effective dose of radiation to an individual in need to improve or enhance the effect of an equal dose of the same radiation upon a cancer or a tumor in an individual in need.

To be more specific, "to improve or enhance the effect of the therapeutically active composition upon a cancer or a tumor in an individual in need" or "to improve or enhance the effect of an equal dose of the same radiation upon a cancer or a tumor in an individual in need" used herein refer to improving, enhancing or intensifying the cytotoxicity of the therapeutically active composition or a radiation to a cancer, a cancer cell, a variant cell, a tumor cell or a combination thereof, to decrease the resistance of a cancer cell or various type of the abovementioned cells to the therapeutically active composition or the radiation, to induce apoptosis of a cancer cell or various type of the abovementioned cells initiated by the therapeutically active composition or the radiation, or the combination of the above, by using the aforementioned composition through, for example, specific biochemical reactions or signal transduction pathways (such as phosphorylation of a specific protein).

As used herein, "an effective amount" refers to an amount of the materials or the compounds mentioned, which can effectively inhibit, treat the syndromes of a cancer or retard or reverse the rate of tumor proliferation or prevent the formation of a cancer or a tumor. And "an effective dose" refers to the dose value of the radiation mentioned, which can also accomplish the effects aforementioned after being absorbed by a living tissue.

As used herein, "a therapeutically active composition" refers to one or more natural material or a product obtained from processing a nature material, or a synthesized compound, wherein within the effective dose range, it can perform treatment or prevention effects on specific diseases, adjustment disorders or indicants by changing the physiological condition of the subject received administration. For example, the therapeutically active composition can be a compound, preferably one or more small molecular composite, an antibody, an antibody-drug complex or a combination thereof. Specifically, a therapeutically active composition can be, for example, an alkylating agent including nimustine, a metabolite including fluorouracil (5-FU) and a heavy metal including cisplatin.

In particular, as used herein, "administration together" refers to administrating the combination of rapamycin and substituted quinoline before, during or both before and during the application of the therapeutically active composition. Specifically, for example, to administrate with the therapeutically active composition at the same time within the same treating procedure, to separately administrate at different but close points of time within a day, or even to administrate individually before the application of the therapeutically active composition in a different day with its effect maintained.

As used herein, "an individual in need" refers to an animal suffering from a cancer, having a tumor formed in its body, having the symptoms of a cancer or a tumor, having a tendency of suffering from a cancer, or having a tumor formed inside of its body. Said animal includes mammals and preferably refers to humans.

After administrating to an individual in need, the rapamycin and the substituted quinoline cause a synergistic effect, and therefore performs a further remarkable sensitizing effect comparing to when the rapamycin or the substituted quinoline is used individually. In addition, although rapamycin and substituted quinoline have been used as therapeutically active composition in the prior art, i.e. an anti-cancer or anti-tumor drug, but the treatment effects of both are quite limited. The applicant discovers that the combination of rapamycin and substituted quinoline is not suitable for acting as an active composition providing treatment effects in a treatment procedure, but should be playing an assisting part therein, which is, the cancer therapy sensitizer disclosed in the present invention, preferably a sensitizer for a chemical treatment or a radiation treatment.

[Treating Subjects and Administration Pathways]

The combination of rapamycin and substituted quinoline according to the present invention can be applied in any form of cancer therapies of a cancer or a tumor, and is especially suitable for the application on, for example, lung cancer, colon cancer or breast cancer; particularly suitable for all kinds of solid cancers, to treat a tumor, retard the growth of a tumor or prevent the formation of a tumor.

The combination of rapamycin and substituted quinoline of the present invention can be formed in, for example but not limited to, a solid or liquid oral administration dosage form, such as a tablet or a capsule, preferably produced together with an effective amount of therapeutically active composition into an oral administrative tablet. Of course, it can also be formed as other available dosage forms, such as pills, sachets, granules, powders, chewing gums, suspensions, emulsions, suppositories and solutions.

Other than oral administration, the combination of rapamycin and substituted quinoline can also be administrated via a pathway outside the gastrointestinal tract, for example but not limited to, intravenous injection, or subcutaneous, intramuscular, intrathecal, intraperitoneal, intrarectal, viginal, nasal, intragastric, intratracheal, pulmonary, intratumoral or peritumoral injection or implantation. On the other hand, when the cancer therapy is, for example, a chemical treatment, all the pathways stated above may be used as administration pathways of the combination and a therapeutically active composition together or individually.

To sum up, the cancer therapy sensitizer, pharmaceutical composition, kit and use of the present invention apply the combination of rapamycin and substituted quinoline to increase the sensitization of a cancer cell or a tumor, thereby when applying in cooperation with a therapeutically active composition, they can achieve the goal of improving or increasing the effect of the therapeutically active composition upon a cancer or a tumor in an individual in need.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

Figure 1:
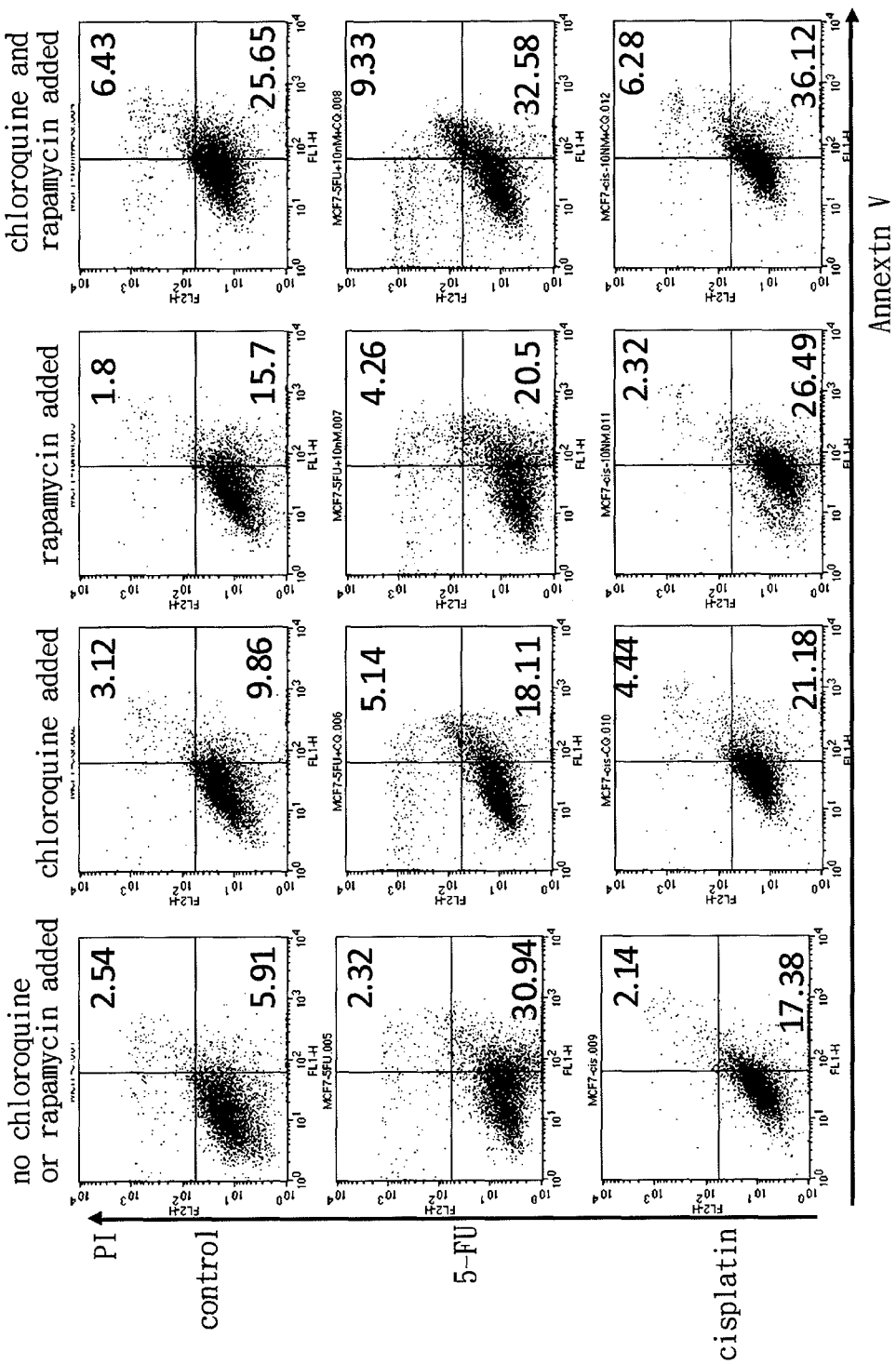
FIG. 1 is the dot data map of apoptosis under the individual reactions of 5-FU and Cisplatin in Experimental Example 2 analyzed by a Flow cytometer.

The present invention will be apparent from the following detailed description, which proceeds with reference to the accompanying drawings, wherein the same references relate to the same elements. The ratio and usage of rapamycin, substituted quinoline and the combination thereof can be referred to the paragraphs above and thus will not be re-illustrated here.

A cancer therapy sensitizer according to the present invention comprises rapamycin and substituted quinoline. In the present embodiment, the rapamycin is a compound of Formula I described above, and the substituted quinoline is chloroquine.

The method of preparing rapamycin and substituted quinoline is well-known by a person having ordinary skill in the art. Further, it is easy to understand the technique of producing a cancer therapy sensitizer with both rapamycin and substituted quinoline. In the present embodiment, a cancer sensitizer can further include a pharmaceutically acceptable carrier, diluent, excipient or a combination thereof for preparing a compatible dosage form or prescription form, wherein the pharmaceutically acceptable carrier, diluent or excipient can be, for example, well-known magnesium carbonate, magnesium stearate, talc, sugar, lactose or a combination thereof.

The preparation of a cancer therapy sensitizer is not limited to uniformly mixing rapamycin and substituted quinoline, that is, in cancer therapy sensitizers with the same dosage form, rapamycin and substituted quinoline can be mixed in other ratio, or even not being mixed. For example, a cancer therapy sensitizer can be a tablet or a capsule, wherein part of it being rapamycin and another part of it being substituted quinoline. Preferably, in the present embodiment, rapamycin and chloroquine can be bought from a vendor (please refer to the experimental examples), and a cancer therapy sensitizer can be powders prepared by mixing powdery rapamycin and substituted quinoline.

Generally speaking, one with ordinary skill in the art can easily know the compatible dose range of rapamycin and substituted quinoline, which is also the compatible dose range of the present invention. For example, the acceptable dose range of rapamycin for an individual in need is between about 0.001 mg and about 1000 mg per kg per day, and the acceptable dose range of substituted quinoline for an individual in need is between about 0.001 mg and about 1000 mg per kg per day. Preferably, the dose range of rapamycin is between about 0.1 mg and about 100 mg per kg per day, and the dose range of substituted quinoline is about 1.5 mg to about 150 mg per kg per day. Certainly, it is essential for the dose of rapamycin or substituted quinoline to alter according to the therapy method, the administration pathway, or the physiological condition of an individual in need. Generally speaking, oral administration requires higher dose. Generally, it requires relatively lower dose during the primary stage of the treatment.

There may be a dose unit of a cancer therapy sensitizer in every formulation, that is, one formulation contains enough dose for performing sensitizing effect in an individual in need, as is convenient for direct administration. In the present embodiment, every package of powders contains a dose unit of cancer therapy sensitizer. Needless to say, in other embodiments of the present invention, one dose unit of a cancer therapy sensitizer can be separated into several sub-dose units or sub-packages, for example, separated into two to three tablets or capsules and packed in the same blister pack.

In the present embodiment, the cancer therapy sensitizer is produced independently and thus can be administrated independently. In a chemical treatment, for example, a cancer therapy sensitizer can be applied before, during or both before and during a treatment procedure. To be specific, a cancer therapy sensitizer can be administrated with the therapeutically active composition at the same time or at a different time of the day, for example, with an interval of 1 or 5 hours. Similarly, in a radiation treatment, a cancer therapy sensitizer can also be applied before, during or both before and during the application of radiation.

Besides, in whichever cancer therapy method, the frequency and order of administration of a cancer therapy sensitizer are not limited. In the present aspect, during one chemical treatment procedure, only one administration of a cancer therapy sensitizer is required. And in other aspects, a cancer therapy sensitizer is provided every time before the administration of a therapeutically active composition, or a cancer therapy sensitizer is re-administered during the period of every two, three or five times of administration of a therapeutically active. However, the present invention is not limited to this.

However, specifically, in other aspects of the present embodiment, a cancer therapy sensitizer can also be processed together into a pharmaceutical composition, that is, this pharmaceutical composition contains a single dosage of a cancer therapy sensitizer and an effective amount of therapeutically active composition, like a tablet or powders, which is beneficial, for example, for providing the treatment to specific cancers and thus has different orientation from the aforementioned cancer therapy sensitizer which is made and administrated independently and thus has larger application flexibility. In the present embodiment, the ratio of the cancer therapy sensitizer and the therapeutically active composition can be from 1000:1 to 0.1:1, preferable 100:1 to 1:1. Of course, said ratio can be adjusted according to the subject received administration, its physiological condition and the type of cancer. As for the method of preparing the pharmaceutical composition, the dosage form and the composition besides the cancer therapy sensitizer can all be completed by one with ordinary skill in the art according to the disclosure of the present invention.

Further, in the present embodiment, when a cancer therapy sensitizer is used before, during or both before and during the application of a cancer therapy, rapamycin and substituted quinoline can cause a synergistic effect to improve or enhance the effect of one or more effective amount of cancer therapy methods upon a cancer or a tumor in an individual in need and then achieve the goal of eliminating, inhibiting, improving, comforting or preventing a cancer and its symptoms; retarding, prohibiting, reversing the rate of tumor proliferation; or the medical effects similar to the foregoing goals, especially to improve, enhance or intensify the cytotoxicity of the therapeutically active composition to a cancer, a cancer cell, a variant cell, a tumor cell or a combination thereof, to decrease the resistance of a cancer cell or various type of the abovementioned cells to the cancer therapy method, to induce apoptosis of a cancer cell or various type of the abovementioned cells initiated by the therapeutically active composition, or the combination of the above. Among which, the cancer therapy methods abovementioned can be exemplified, but not limited to, providing an effective amount of therapeutically active composition or providing an effective dose of radiation.

In yet another embodiment, the present invention provides another cancer therapy sensitizer kit. Similarly, a cancer therapy may be a chemical treatment or a radiation treatment and it may applied together with an effective amount of therapeutically active composition or an effective dose of radiation to an individual in need. Among which, the cancer therapy sensitizer kit includes a rapamycin, a first pharmaceutically acceptable carrier, diluent or excipient, a substituted quinoline and a second pharmaceutically acceptable carrier, diluent or excipient. The related description of the rapamycin, the substituted quinoline and the rest can be referred to in the paragraphs above and thus will not be re-illustrated here. Only the insufficient or unexplained parts will be further illustrated.

The first and the second pharmaceutically acceptable carrier, diluent, excipient or a combination thereof can be a well-known material or composition in the art, and the method and dosage form of preparing a prescription of each of them with rapamycin or substituted quinoline are also prior art in the field of the present invention. In particular, in the present embodiment, there can be an individual pack or container, such as a blister pack, for a cancer therapy sensitizer kit, to contain or store, for example, the tablet made of rapamycin and a first pharmaceutically acceptable excipient and the tablet made of substituted quinoline and a second pharmaceutically acceptable excipient. Said individual pack can be provided to an individual in need during application or be administrated to an individual in need after preparation.

Needless to say, in other embodiments, the rapamycin and the substituted quinoline can be processed together into an injection form, which is obtained by preparing according to a specific ratio at the time of the application of a cancer therapy or within a suitable time period before the application, for example, within one to several weeks (such as within 10 days, 5 days or 24 hours). Accordingly, when rapamycin and substituted quinoline need to be administrated separately, in different dosage forms, or when the compositional ratio of which needs to be adjusted, it is especially beneficial to use the cancer therapy sensitizer kit of the present invention.

In yet another embodiment, the present invention provides a use of a combination of rapamycin and quinoline as a sensitizer, wherein the related description of the rapamycin, the substituted quinoline and other parts can be referred to in the paragraphs above and thus will not be re-illustrated here.

As mentioned above, according to the cancer therapy sensitizer, kit and use of the present invention, a combination of rapamycin and substituted quinoline is used to increase the sensitivity of cancer cells, variant cells or tumors and therefore achieving the improvement or enhancement of the effect of the therapeutically active composition or the radiation upon a cancer or a tumor in an individual in need.

Experimental Example 1

To Prepare the Cancer Therapy Sensitizer

The rapamycin and chloroquine used in the present invention were purchased individually from Sigma-Aldrich, Inc, St. Louis, Mo., USA. Obtain about 1 mg of rapamycin and about 2 g of substituted chloroquine by a weighting scale in room temperature, mix the powder rapamycin and chloroquine uniformly in a weight percentage ratio of 1:2000. And then, pack it into a dosage form of powders or sachets and store in room temperature.

Experimental Example 2

Using the Cancer Therapy Sensitizer to Enhance the Effect of 5-FU upon the Apoptosis of a Cancer Cell Culture breast cancer cell line MCF-7 by tissue culture technique in DMEM supplemented with 10% FBS to a proper amount. And then, take a suspension containing $1 \times 10^6$ cells and inoculate it in a 6-wells plate. In addition, prepare 10 nM rapamycin, 10 μM chloroquine, 5 μM 5-FU and 5 μM Cisplatin solution separately in room temperature. Similarly, add rapamycin and chloroquine in room temperature in sequence, and then add 5-FU or Cisplatin separately. Put the plate into a 37° C. incubator to continue culturing for 48 hours. Remove the broth and chemical in each well in sequence, add PBS to wash, and then use trypsin-EDTA to obtain cells and analyze the apoptosis.

Apoptosis is analyzed by the method of phosphatidylserine externalization using an analysis kit for apoptosis, Annexin V (BD Pharmingen), the procedures are in accordance with the manual. In summary, wash the obtained MCF-7 cells with PBS for 3 times, and use Annexin V/propidium iodide (PI) to dye part of the cells. Add 1% BSA to those cells that have been treated and then add 222.5 μl binding buffer; dye directly with 10 μl PI and 2.5 μl Annexin V-FITC, and immediately move the reaction to an environment with low temperature and no light for 10 minutes. Calculate the percentage of apoptosis by a Flow cytometer and its software, FACSCalibur.

FIG. 1 is the dot data map of apoptosis under the individual reactions of 5-FU and Cisplatin in Experimental Example 2 analyzed by a Flow cytometer. Referring to FIG. 1, the procedure of each data map is as stated above, only that "Control," "5-FU," and "Cisplatin" marked along the longitudinal axis individually represent "no therapeutically active composition added," "5-FU added" and "Cisplatin added;" "no chloroquine or rapamycin added" marked on the horizontal axis represents "neither compound is added;" "chloroquine added" or "rapamycin added" individually represent only chloroquine or only rapamycin is added, and "chloroquine and rapamycin added" means both of the two compounds are added.

For a single data map, the PI coloring distribution of cells after the reaction of compounds is shown along the longitudinal axis, and the Annexin V coloring distribution is shown along the horizontal axis. It is clear from the data result, comparing to the distribution pattern of control, in a chemical therapy experiment using whether 5-FU or Cisplatin as the active composition, although using chloroquine or rapamycin alone as the sensitizer helps to raise the ratio of apoptosis, but only in a limited degree (for example, the four groups of experiments of Cisplatin), or even decrease the original effect (for example, the four experiments of 5-FU). However, if the combination of chloroquine and rapamycin is added, the apoptosis ratio is remarkably increased operated in cooperation with whichever active composition.

Experimental Example 3

Using the Cancer Therapy Sensitizer to Enhance the Effect of 5-FU upon Inhibiting the Growth Rate of a Tumor in an Animal Model Culture colon cancer cell line LS174T by tissue culture technique to a proper amount, obtain cancer cells by trypsin-EDTA and continue with suspending it in DMEM supplemented with 10% FBS and 0.7 mg/ml G418 to a proper amount. And then, take 250 g for 10 minutes of spinning centrifugal, and then re-suspend it with a cell culture media and obtain a suspension containing $1 \times 10^7$ cells for subcutaneous transplantation of a mouse.

Choose four to six-week-old female mice of severe combined immunodeficiency, BALB/c. SCID, inject $1 \times 10^5$ LS 174T cells in the right fossa paralumbar those mice with a 27-gauge needle connecting to a tuberculin syringe with the capacity of 1 ml. After about 12 days, when the tumor size reaches a diameter of 4 mm, randomly separate the mice into 4 groups to receive administration of different compounds including hydrochloric acid as control, 5-FU solution, the combinational solution of chloroquine and rapamycin and the combination solution of 5-FU, chloroquine and rapamycin. Among which, the manner of administration and the dose of injection are described as the following: PBS or a 5-FU solution with a density of 40 mg/kg by intravenous injection; a rapamycin solution with a density of 5 mg/kg and a chloroquine solution with a density of 50 mg/kg by intrapentoneal injection; each solution is administrated once every day and five times a weeks.

Measure two diameters which are orthonormal and being the longest (a) and the wildest (b), calculate the volume of the tumor with the formula of $V = \frac{1}{2}a^2 b$. When the diameter of the tumor of control group which received PBS reaches 2 cm, anatomize the mice to observe.

Figure 2:
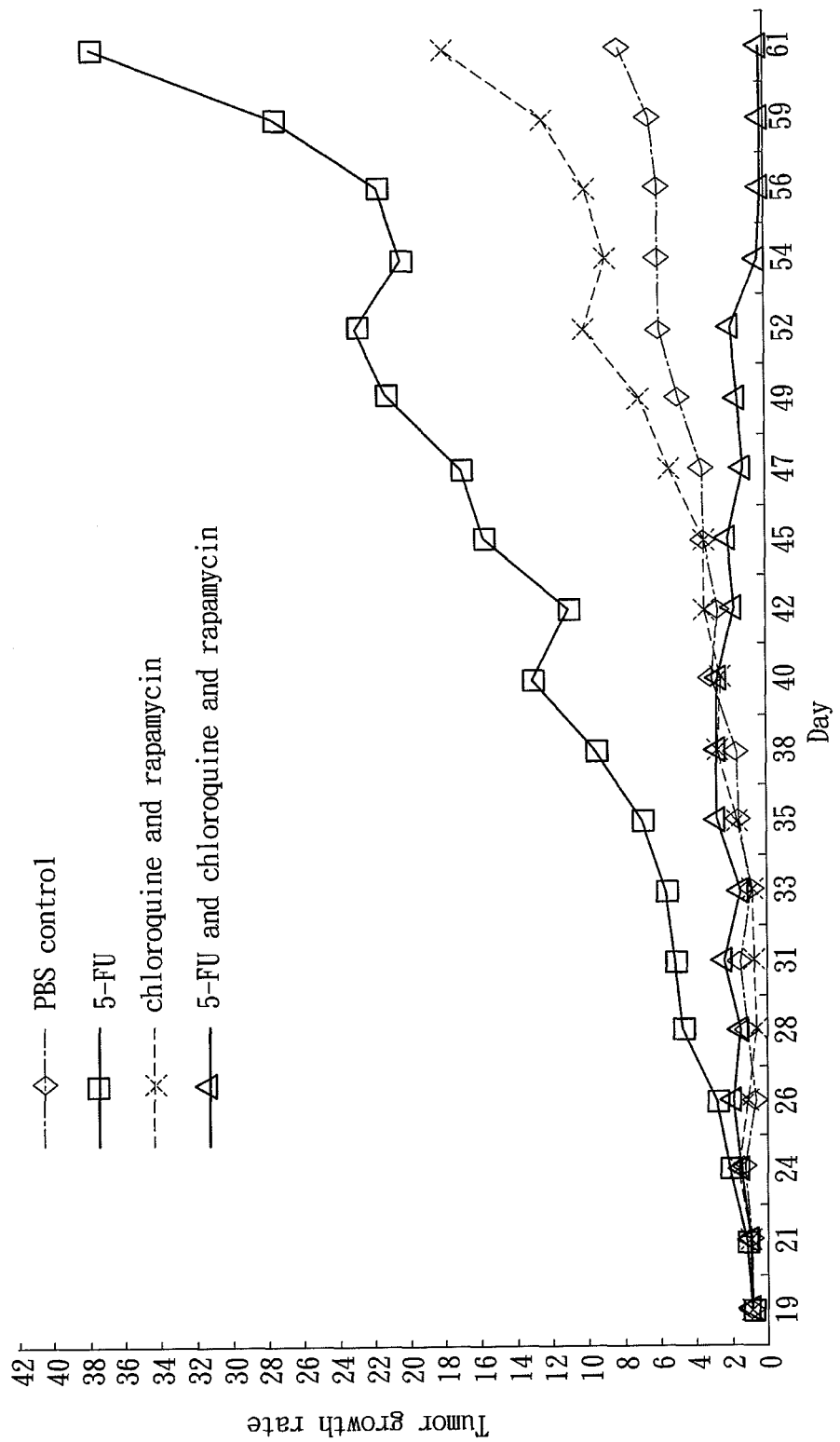
FIG. 2 is the data map of the growth rate of tumor in each group of animal models of Experimental Example 3.

FIG. 2 is the data map of the growth rate of tumor in each group of animal models of Experimental Example 3. Please refer to FIG. 3, when each group has been operated, anatomized and observed in the manner narrated above, we find out that using the combination of chloroquine and rapamycin together with 5-FU can remarkably inhibit the growth of a tumor, and a tumor even stopped expending 54 days after the operation. Comparing to adding PBS or other two groups of control which use them separately, the sensitizing effect upon the active composition when the two compounds are used together has been proved.

Experimental Example 4

Using the Cancer Therapy Sensitizer to Enhance the Effect of a Radiation upon the Apoptosis of a Cancer Cell Culture colon cancer cell line LS174T and epidermoid carcinoma cell line A431 by tissue culture technique in DMEM supplemented with 10% FBS to a proper amount. Following, obtain a suspension containing $1 \times 10^6$ cells and inoculate it in a 6-wells plate. Complete the formulation of 10 nM rapamycin and 10 μM chloroquine in room temperature and add the rapamycin and the chloroquine simultaneously to the plate. Put the plate into a 37° C. incubator to continue culturing for 24 hours and then irradiate the cells with a radiation with a dose of 8 Gy for one minute.

After the irradiation of the radiation, continue to culture for 48 hours in a 37° C. incubator. And then, use the same kit and steps stated in Experimental Example 2 to analyze the apoptosis.

Figure 3:
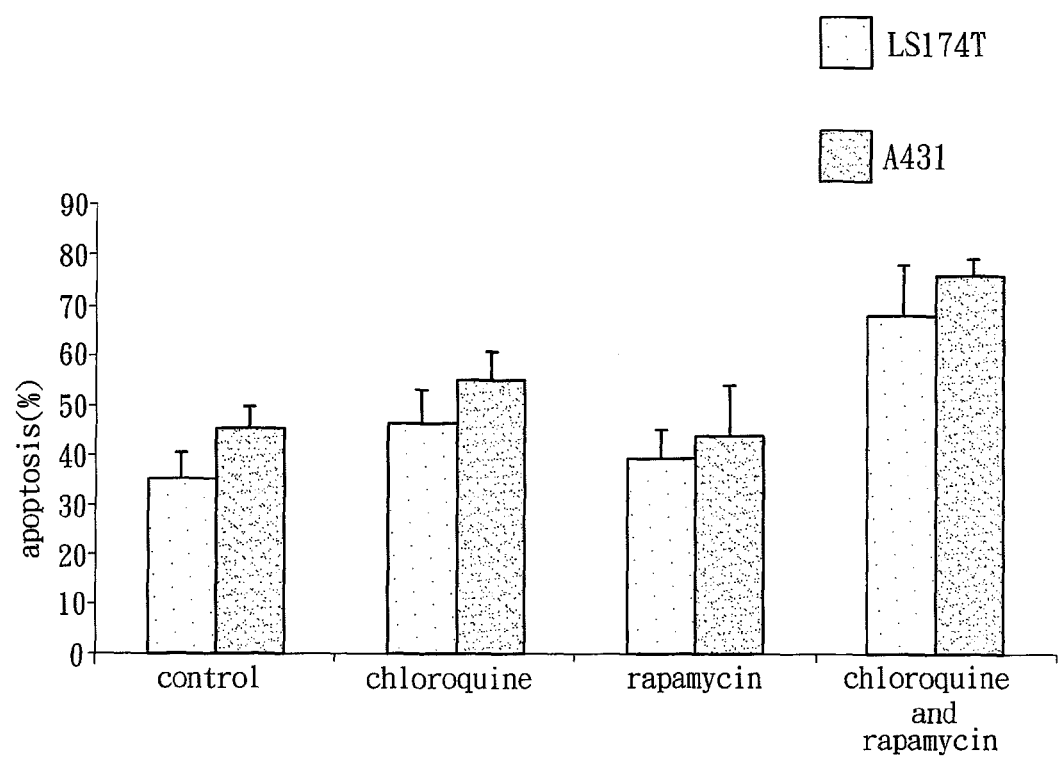
FIG. 3 is the data map of apoptosis result under the reaction of a radiation in Experimental Example 4 analyzed by a Cytometer.

FIG. 3 is the data map of apoptosis result under the reaction of a radiation in Experimental Example 4 analyzed by a Cytometer. Referring to FIG. 3, it is clear from the data result, the combination of chloroquine and rapamycin can remarkably raise the apoptosis ratio of LS174T or A431 cells by the radiation, in a degree of over 30% and close to 35%, which prevails control groups of not using or using the compounds separately.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A cancer therapy sensitizer, comprising rapamycin and substituted quinoline, wherein the cancer therapy sensitizer applied in breast cancer, colon cancer and epidermoid carcinoma.

2. The cancer therapy sensitizer of claim 1, wherein the rapamycin is a compound of the following formula:

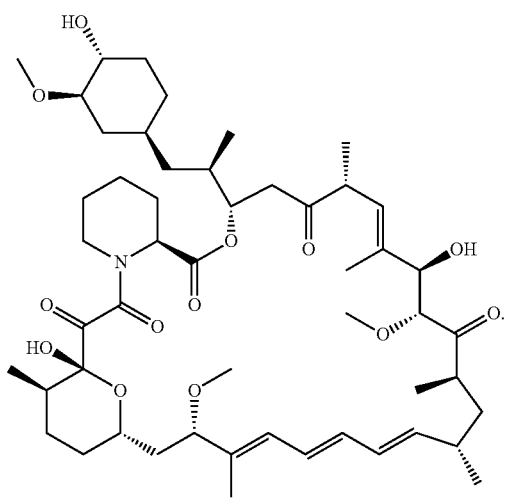 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

3. The cancer therapy sensitizer of claim 1, wherein the substituted quinoline is a chloroquine.

4. The cancer therapy sensitizer of claim 1, wherein the weight percentage ratio of the rapamycin to the substituted quinoline is 1:100 to 1:5000.

5. The cancer therapy sensitizer of claim 1, wherein the rapamycin and the substituted quinoline cause a synergistic effect.

6. The cancer therapy sensitizer of claim 1, wherein the cancer therapy is a radiation treatment or a chemical treatment.

7. A method of treating cancers, comprising:
using a cancer therapy sensitizer, wherein when the cancer therapy is a chemical treatment, the cancer therapy sensitizer of claim 6 is administrated together with an effective amount of therapeutically active composition to an individual in need thereof.

8. The method of claim 7, wherein the cancer therapy sensitizer is administrated together with the effective amount of therapeutically active composition to improve or enhance the effect of the therapeutically active composition to a cancer or a tumor in the individual in need thereof.

9. A cancer therapy sensitizer kit comprising:
rapamycin and a first pharmaceutically acceptable carrier, diluent, excipient, or a combination thereof; and
substituted quinoline and a second pharmaceutically acceptable carrier, diluent, excipient, or a combination thereof,
wherein the cancer therapy sensitizer applied in breast cancer, colon cancer and epidermoid carcinoma.

10. The cancer therapy sensitizer kit of claim 9, wherein the rapamycin is a compound of the following formula:

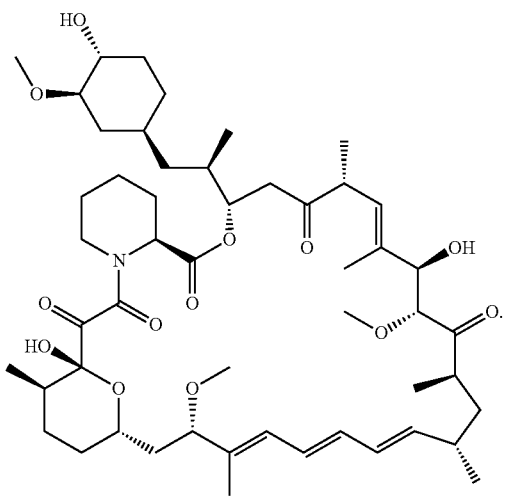 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

11. The cancer therapy sensitizer kit of claim 9, wherein the substituted quinoline is a chloroquine.

12. The cancer therapy sensitizer kit of claim 9, wherein the rapamycin and the substituted quinoline cause a synergistic effect.

13. The cancer therapy sensitizer kit of claim 9, wherein the cancer therapy is a radiation treatment or a chemical treatment.

14. A method of treating cancers, comprising:
using a cancer therapy sensitizer kit, wherein when the cancer therapy is a chemical treatment, the cancer therapy sensitizer kit of claim 13 is applied together with an effective amount of therapeutically active composition to an individual in need thereof.

15. The method of claim 14, wherein the cancer therapy sensitizer kit is applied together with the effective amount of therapeutically active composition to improve or enhance the effect of the therapeutically active composition to a cancer or a tumor in the individual in need thereof.

16. A method of treating cancers, comprising:
using a combination of a rapamycin and a substituted quinoline as a cancer therapy sensitizer, wherein the cancer therapy sensitizer applied in breast cancer, colon cancer and epidermoid carcinoma.

17. The method of claim 16, wherein the rapamycin is a compound of the following formula:

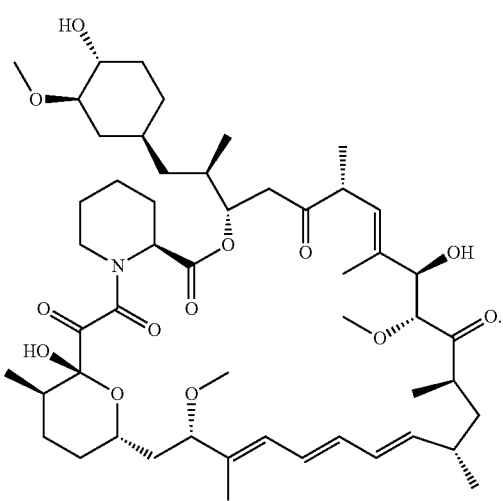 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

18. The method of claim 16, wherein the substituted quinoline is a chloroquine.

19. The method of claim 16, wherein the weight percentage ratio of the rapamycin to the substituted quino line is between 1:100 and 1:5000.

20. The method of claim 16, wherein the rapamycin and the substituted quinoline cause a synergistic effect.

21. The method of claim 16, wherein the cancer therapy is a radiation treatment or a chemical treatment.

22. The method of claim 21, wherein when the cancer therapy is a chemical treatment, the cancer therapy sensitizer is administrated together with an therapeutically active composition to an individual in need.

23. The method of claim 22, wherein the cancer therapy sensitizer is administrated together with a therapeutically active composition to improve or enhance the effect of the therapeutically active composition to a cancer or a tumor in the individual in need.

24. The method of claim 16, wherein the combination of the rapamycin and the substituted quinoline is administrated before, during or before and during the cancer therapy.

25. The method of claim 16, wherein the cancer therapy sensitizer is used for treating a solid tumor.

26. The method of claim 16, wherein the cancer therapy sensitizer is a solid oral administration or a liquid oral administration.

* * * * *